(12) United States Patent
Tsujihara et al.

(10) Patent No.: US 6,512,118 B1
(45) Date of Patent: *Jan. 28, 2003

(54) CAMPTOTHECIN DERIVATIVES

(75) Inventors: Kenji Tsujihara, Urawa (JP); Takayuki Kawaguchi, Tokyo-to (JP); Satoshi Okuno, Misato (JP); Toshiro Yano, Urawa (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/227,158

(22) Filed: Jan. 8, 1999

Related U.S. Application Data

(62) Division of application No. 08/773,182, filed on Dec. 27, 1996, now Pat. No. 5,892,043.

(30) Foreign Application Priority Data

Dec. 28, 1995 (JP) ............................................. 7-343575
Jul. 30, 1996 (JP) ............................................. 8-200105

(51) Int. Cl.[7] ........................................... C07D 471/00
(52) U.S. Cl. ..................... 546/48; 514/279; 514/283; 514/2; 514/18; 514/19; 530/333; 530/322
(58) Field of Search ........................... 546/48; 514/279, 514/283, 2, 18, 19; 530/333, 322

(56) References Cited

FOREIGN PATENT DOCUMENTS

| EP | 0220601 | 5/1987 |
| EP | 0640622 | 3/1995 |

OTHER PUBLICATIONS

Wani, J. Med. Chem., 29, 2358, 1986.
Kingsbury, J. Med. Chem., 34, 98, 1991.
Abstract of Japanese Document 1–279891, Abstract No. 89–001081/01 (Nov. 10, 1989).
Abstract of Japanese Document 5–222048, Abstract No. 93–145471/18 (Aug. 31, 1993).
Abstract of Japanese Document 6–87746, Abstract No. 94–140950/17 (Mar. 29, 1994).
Abstract of Japanese Document 6–228141, Abstract No. 93–265987/34 (Aug. 16, 1994).
Abstract of Japanese Document 4–503505, Abstract No. 90–132098/17 (Apr. 15, 1993).
Abstract of Japanese Document 5–502017, Abstract No. 91–117470/16 (Jun. 25, 1992).
Zhang et al., *Chemical Abstracts*, vol. 110, No. 12, Mar. 20, 1989, p. 413, col. 2, Abstract No. 101605w.

Primary Examiner—David Lukton
(74) Attorney, Agent, or Firm—Birch, Stewart, Kolasch & Birch, LLP

(57) ABSTRACT

A camptothecin derivative comprising a compound of the formula [I] is disclosed:

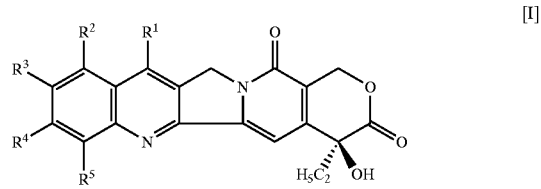

wherein $R^1$, $R^2$, $R^3$, $R^4$ and $R^5$ are (A) adjacent two groups combine to form alkylene, or both are H, and one of the remaining three groups is $-X_n-Alk_m-R^6$, and the other two are H, alkyl or halogen, or (B) adjacent two groups combine to form alkylene, and one of the carbon atoms of said alkylene group is substituted by $-X_n-Alk_m-R^6$, and the remaining three groups are H, alkyl or a halogen, and one or two $-CH_2-$ of the alkylene in (A) or (B) may optionally be replaced by $-O-$, $-S-$ or $-NH-$, X is $-O-$ or $-NH-$, Alk is alkylene, $R^6$ is $-NH_2$,

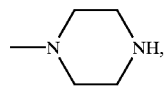

or $-OH$, m and n are both 0 or 1, or m is 1 and n is 0, which camptothecin compound is bound to a polysaccharide having carboxyl groups via an amino acid or a peptide, or a pharmaceutically acceptable salt thereof. Said camptothecin derivatives show enhanced antitumor activities but few side effects and are useful as a medicament.

12 Claims, No Drawings

CAMPTOTHECIN DERIVATIVES

This application is a divisional of Ser. No. 08/773,182, filed Dec. 27, 1996 now U.S. Pat. No. 5,892,043.

TECHNICAL FIELD

The present invention relates to a novel camptothecin derivative having enhanced antitumor activities. More particularly, the present invention relates to a novel camptothecin derivative which is prepared by combining an aminoalkoxy- or hydroxyalkoxy-camptothecin compound with a polysaccharide having carboxyl groups via an amino acid or a peptide, and a process for preparing the same. The camptothecin derivatives of the present invention can be delivered into a target region of the patient selectively and in much amount, so that they can show desired pharmacological activities at the desired region of the patient. Therefore, the antitumor activities of the camptothecin compounds are enormously enhanced and their side effects can be reduced, and hence, the camptothecin derivatives of the present invention are extremely useful as a medicaments.

PRIOR ART

Camptothecin is one plant alkaloids, and has the following formula:

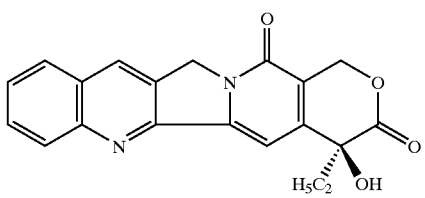

and it has been known to show antileukemic and antitumor activities, and one camptothecin derivative, irinotecan hydrochloride {CPT-11, 7-ethyl-1-[4-(piperidino)-1-piperidino]carbonyloxycamptothecin}, has already been put on the market. However, CPT-11 shows potent antitumor activities in clinical use but also shows severe toxicity like other antitumor agents, so that CPT-11 has been restricted in its therapeutic use [cf. Cancer and Chemotherapy, vol. 21, p. 709 (1994)].

There have been synthesized various camptothecin compounds, and it has been reported that these camptothecin compounds show antitumor activities (Japanese Patent First Publication (Kokai) Nos. 279891/1989, 222048/1993, 87746/1994, 228141/1994, and Japanese Patent First Publication (Kohyo) Nos. 503505/1992, 502017/1992).

On the other hand, in order to enhance antitumor activities and also to reduce the side effects thereof as low as possible, these compounds having such severe side effects have been studied as to a kind of drug delivery system therefor, by which a necessary amount of a drug is selectively delivered into a target tissue. Especially, in the chemotherapy of cancers, it is a serious problem that there is no significant difference between tumor cells and normal cells in sensitivity against anticancer agents, and many studies on targeting-type drug delivery system for anticancer agents have been done in order to selectively deliver an anticancer agent into a cancer-bearing region, for example, doxorubicin-polysaccharide complex (WO 94/19376), doxorubicin-inclusive liposome (Enhancement of effects of anticancer agents and targeting therapy, p. 227 (1987), published by Science Forum Ltd.), dextran-binding mitomycin (Enhancement of effects of anticancer agents and targeting therapy, p. 278 (1987), published by Science Forum Ltd.).

As explained above, camptothecin compounds show excellent anti-tumor activities and are very useful as a medicament but they are strictly restricted in clinical use because of their severe side effects. Thus, it is desired to develop a new camptothecin derivative wherein the excellent pharmacological activities of camptothecin compounds are duly retained but undesirable severe side effects are suppressed.

Under the above mentioned circumstances, the present inventors have intensively studied in order to obtain an excellent camptothecin derivative without the drawback of the conventional camptothecin compounds by utilizing the techniques of the above mentioned drug delivery system, and finally have found that a novel camptothecin derivative having desired pharmacological effects can be obtained by combining a camptothecin compound having a reactive group with a polysaccharide having carboxyl groups via an amino acid or a peptide, and have accomplished the present invention.

BRIEF DESCRIPTION OF INVENTION

An object of the present invention is to provide a novel camptothecin derivative comprising the camptothecin compound [I] bound to a polysaccharide having carboxyl groups via an amino acid or a peptide, which has enhanced antitumor activities with less side effects.

Another object of the present invention is to provide a process for preparing these camptothecin derivative.

DETAILED DESCRIPTION OF INVENTION

The compound of the present invention is a camptothecin derivative comprising a camptothecin compound having an aminoalkoxy group or a hydroxyalkoxy group, represented by the formula [I]:

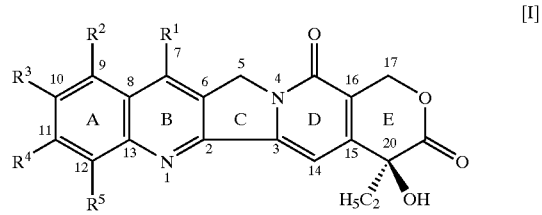

wherein $R^1$, $R^2$, $R^3$, $R^4$ and $R^5$ are (A) among $R^1$, $R^2$, $R^3$, $R^4$ and $R^5$, two groups being adjacent each other combine to form an alkylene group, or both are a hydrogen atom, and one of the remaining three groups of $R^1$, $R^2$, $R^3$, $R^4$ and $R^5$ is a group of the formula: $-X_n$-$Alk_m$-$R^6$, and the other two groups are a hydrogen atom, an alkyl group or a halogen atom, or (B) among $R^1$, $R^2$, $R^3$, $R^4$ and $R^5$, two groups being adjacent each other combine to form an alkylene group, and one of the carbon atoms of said alkylene group is substituted by a group of the formula: $-X_n$-$Alk_m$-$R^6$, and the remaining three groups of $R^1$, $R^2$, $R^3$, $R^4$ and $R^5$ are a hydrogen atom, an alkyl group or a halogen atom, and one or two methylene groups of the alkylene group in (A) or (B) may optionally be replaced by —O—, —S— or —NH—, X is —O— or —NH—, Alk is an alkylene group, $R^6$ is —$NH_2$, a group of the formula:

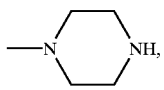

or —OH, m and n are both 0 or 1, or m is 1 and n is 0, which camptothecin compound is bound to a polysaccharide having carboxyl groups via an amino acid or a peptide. The camptothecin derivative of the present invention shows extremely potent antitumor activities but show low toxicity.

The camptothecin derivative of the present invention includes compounds which are prepared by combining the camptothecin compound [I] with a polysaccharide having carboxyl groups via an amino acid or a peptide. For example, such camptothecin derivatives may be prepared by combining a part or all of the carboxyl groups of an amino acid or a peptide with $R^6$ of the compound [I] through acid-amide or ester bonds, followed by combining a part or all of the carboxyl groups of a polysaccharide with amino groups of said amino acid or said peptide through acid-amide bonds. More particularly, the camptothecin derivative of the present invention includes compounds which are prepared by combining the C-terminal carboxyl group of an amino acid or a peptide with $R^6$ of the compound [I] through an acid-amide or ester bond, followed by combining a part or all of the carboxyl groups of a polysaccharide with the N-terminal amino group of said amino acid or said peptide through acid-amide bonds.

Each substituent of the compound of the formula [I] of the present invention is explained below.

The alkylene group in the definition (A) formed by combining adjacent two groups of $R^1$, $R^2$, $R^3$, $R^4$ and $R^5$ each other, wherein one or two methylene groups may optionally be replaced by —O—, —S— or —NH—, is formed by combining each other two substituents at 7- and 9-positions, 9- and 10-positions, 10- and 11-positions, or 11- and 12-positions of the formula [I], and the alkylene group includes a straight chain or branched chain alkylene group having 2 to 6 carbon atoms, for example, ethylene, trimethylene, tetramethylene, pentamethylene, hexamethylene, methylmethylene, methylethylene, methyltrimethylene, etc.

The above alkylene group wherein one of the methylene groups is replaced by —O—, —S— or —NH— includes an alkylene group wherein a methylene group at the end or at any position other than the end is replaced by —O—, —S— or —NH—. For example, such alkylene group includes an alkyleneoxy group represented by the formula: —O-Alk'- (Alk' is an alkylene group, hereinafter, the same) such as methyleneoxy, ethyleneoxy, trimethyleneoxy, tetramethyleneoxy, methylethyleneoxy; an alkyleneamino group represented by the formula: —NH-Alk'- such as methyleneamino, ethyleneamino, trimethyleneamino, tetramethyleneamino, methylethylene-amino; an alkylenethio group represented by the formula: —S-Alk'- such as methylenethio, ethylenethio, trimethylenethio, tetramethylenethio, methylethylenethio; an alkyleneoxy-alkyl group represented by the formula: -Alk'-O-Alk'- such as methyleneoxymethyl, ethyleneoxymethyl, trimethyleneoxymethyl, methylethyleneoxymethyl; an alkyleneaminoalkyl group represented by the formula: -Alk'-NH-Alk'- such as methyleneaminomethyl, ethyleneaminomethyl, trimethyleneaminomethyl, methylethyleneaminomethyl; an alkylenethioalkyl group represented by the formula: -Alk'-S-Alk'- such as methylenethiomethyl, ethylenethiomethyl, trimethylenethiomethyl, methylethylenethiomethyl, and the like.

The above alkylene group wherein two methylene groups are replaced by —O—, —S— or —NH— includes an alkylene group wherein two methylene groups at the ends or at positions other than the ends are replaced by —O—, —S— or —NH—. For example, such alkylene group includes an alkylenedioxy group represented by the formula: —O-Alk'-O— such as methylenedioxy, ethylenedioxy, trimethylenedioxy, tetramethylenedioxy, methylethylenedioxy; an alkylenediamino group represented by the formula: —NH-Alk'-NH— such as methylenediamino, ethylenediamino, trimethylenediamino, tetramethylenediamino, methylethylenediamino; an alkylenedithio group represented by the formula: —S-Alk'-S— such as methylenedithio, ethylenedithio, trimethylenedithio, tetramethylenedithio, methylethylenedithio, and the like.

The Alk in the group of the formula: —$X_n$-$Alk_m$-$R^6$ includes a straight chain or branched chain alkylene group having 1 to 6 carbon atoms, for example, methylene, ethylene, trimethylene, tetramethylene, pentamethylene, hexamethylene, methylethylene, methyltrimethylene, etc. The group of the formula: —$X_n$-$Alk_m$-$R^6$ is, for example, an aminoalkyloxy group (e.g. aminoethyloxy, aminopropyloxy), a piperazinylalkyloxy group (e.g. piperazinylethyloxy, piperazinylpropyloxy, piperazinylbutyloxy, piperazinylpentyloxy), a hydroxyalkyloxy group (e.g. hydroxyethyloxy, hydroxypropyloxy, hydroxybutyloxy, hydroxypentyloxy), an aminoalkylamino group (e.g. aminoethylamino, aminopropylamino, aminobutylamino, aminopentylamino), a piperazinylalkylamino group (e.g. piperazinylethylamino, piperazinylpropylamino, piperazinylbutylamino, piperazinylpentylamino), a hydroxyalkylamino group (e.g. hydroxyethylamino, hydroxypropylamino, hydroxybutylamino, hydroxypentylamino), an aminoalkyl group (e.g. aminomethyl, aminoethyl, aminopropyl, aminobutyl, aminopentyl), a piperazinylalkyl group (e.g. piperazinylmethyl, piperazinylethyl, piperazinylpropyl, piperazinylbutyl, piperazinylpentyl), a hydroxyalkyl group (e.g. hydroxymethyl, hydroxyethyl, hydroxypropyl, hydroxybutyl, hydroxypentyl), amino group, piperazino group, and hydroxy group.

The alkylene group in the definition (B) formed by combining adjacent two groups of $R^1$, $R^2$, $R^3$, $R^4$ and $R^5$ each other, wherein one or two methylene groups may optionally be replaced by —O—, —S— or —NH—, and one of the carbon atoms of said alkylene group is substituted by a group of the formula: —$X_n$-$Alk_m$-$R^6$, is formed by combining each other two substituents at 7- and 9-positions, 9- and 10-positions, 10- and 11-positions, or 11- and 12-positions of the formula [I]. Such alkylene group includes a straight chain or branched chain alkylene group having 2 to 6 carbon atoms, for example, ethylene, trimethylene, tetramethylene, pentamethylene, hexamethylene, methylethylene, methyltrimethylene, etc., and the alkylene group wherein a methylene group or two methylene groups thereof are replaced by —O—, —S— or —NH— are the same ones as those exemplified in the above. Among these alkylene groups, ones wherein one of the carbon atoms is substituted by a group of the formula: —$X_n$-$Alk_m$-$R^6$ are also the same ones as those exemplified in the above.

The lower alkyl group for the remaining groups of $R^1$, $R^2$, $R^3$, $R^4$ and R5 which do not form an alkylene group includes a straight chain or branched chain alkyl group having 1 to 6 carbon atoms, for example, methyl, ethyl, n-propyl, isopropyl, n-butyl, isobutyl, sec-butyl, pentyl, hexyl, etc.

The halogen atom is fluorine, chlorine, bromine or iodine.

Moreover, examples of the partial structure formed by Ring A and Ring B in the above definition (A) of the formula [I] are the following structures:

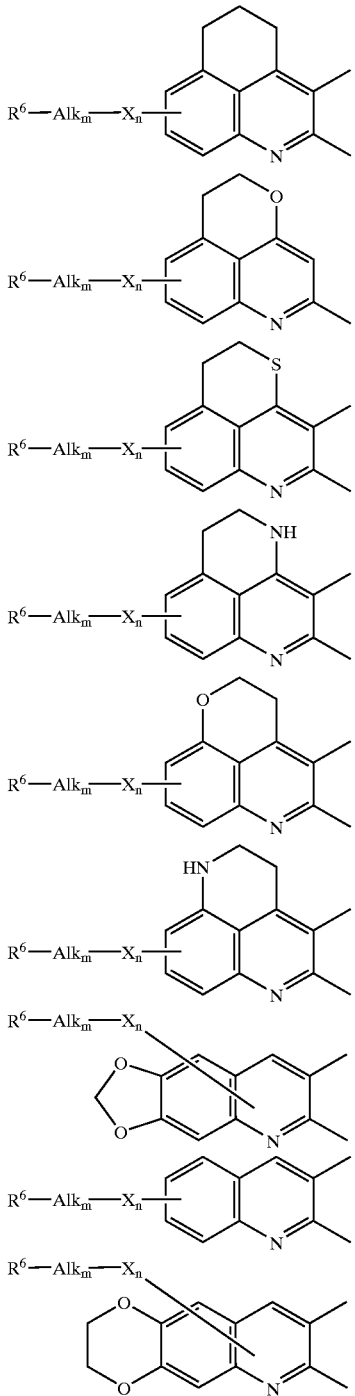

wherein X, Alk, $R^6$, m and n are the same as defined above.

Besides, examples of the partial structure formed by Ring A and Ring B in the above definition (B) of the formula [I] are the following structures:

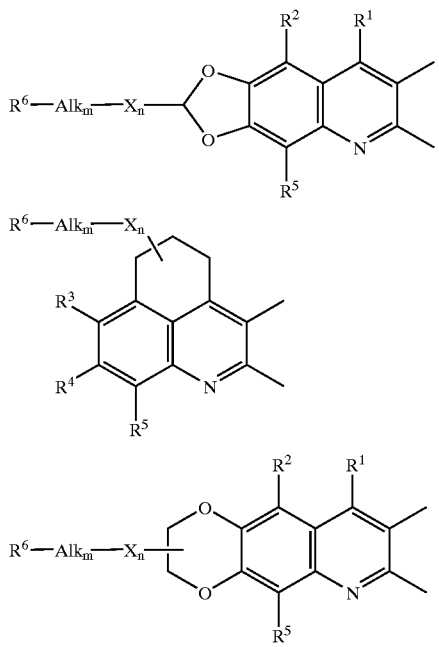

wherein $R^1$, $R^2$, $R^3$, $R^4$ and $R^5$ are each an alkyl group, a halogen atom or a hydrogen atom, and X, Alk, $R^6$, m and n are the same as defined above.

Among them, the preferable combinations of the $R^1$, $R^2$, $R^3$, $R^4$ and $R^5$ are:

(1) $R^1$ and $R^2$ combine to form a trimethylene group, $R^3$ is a 3-aminopropyloxy group, $R^4$ and $R^5$ are each a hydrogen atom:

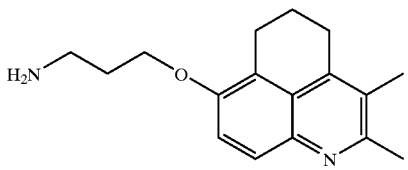

(2) $R^1$ is a piperazinomethyl group, $R^2$ and $R^5$ are each a hydrogen atom, $R^3$ and $R^4$ combine to form an ethylenedioxy group:

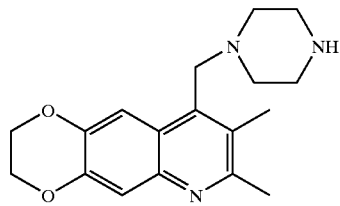

(3) $R^1$ is an aminomethyl group, $R^2$ and $R^5$ are each a hydrogen atom, $R^3$ and $R^4$ combine to form an ethylenedioxy group:

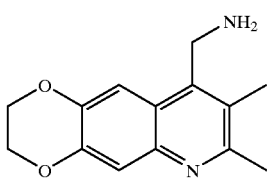

(4) $R^1$, $R^2$, $R^4$ and $R^5$ are each a hydrogen atom, $R^3$ is a 3-aminopropytoxy group:

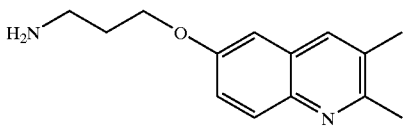

(5) $R^1$ and $R^2$ combine to form an amino-substituted trimethylene group, $R^3$ is a methyl group, $R^4$ is a fluorine atom, $R^5$ is a hydrogen atom:

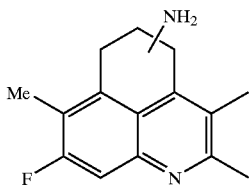

and (6) $R^1$, $R^3$, $R^4$ and $R^5$ are each a hydrogen atom, $R^2$ is an amino group:

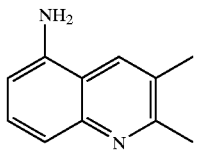

The "polysaccharide having carboxyl groups" of the present invention includes the same as those as disclosed in the above mentioned WO 94/19376, and includes polysaccharides originally having carboxyl groups in the structure thereof (e.g. hyaluronic acid, pectic acid, alginic acid, chondroitin, heparin, etc.), and polysaccharides having originally no carboxyl group (e.g. pullulan, dextran, mannan, chitin, mannoglucan, chitosan, etc.) but being introduced thereto carboxyl groups. Among these polysaccharides, dextran is especially preferable, particularly dextran having an average molecular weight of 20,000 to 400,000 is more preferable, and particularly dextran having an average molecular weight of 50,000 to 150,000 is most preferable (said average molecular weight being determined by Gel permeation chromatography method (GPC analysis), Shinseikagaku Jikken Koza, vol. 20, p. 7). The polysaccharides originally having no carboxyl group but being introduced thereto carboxyl groups mean ones which are prepared by replacing hydrogen atoms of a part or all of hydroxyl groups of polysaccharides originally having no carboxyl group by a carboxy-$C_{1-4}$ alkyl group.

The "polysaccharide having carboxyl groups" of the present invention also includes ones which are prepared by treating a polysaccharide originally having no carboxyl group with a reducing agent, and then followed by replacing hydrogen atoms of a part or all of hydroxyl groups of the product by a carboxy-$C_{1-4}$ alkyl group.

The alkyl moiety of the above carboxy-$C_{1-4}$ alkyl group which replaces the hydrogen atoms of a part or all of hydroxyl groups of polysaccharide may be either a straight chain alkyl group or a branched chain alkyl group. Preferable carboxy-$C_{1-4}$ alkyl group is, for example, carboxymethyl, 1-carboxyethyl, 3-carboxypropyl, 1-methyl-3-carboxypropyl, 2-methyl-3-carboxypropyl, 4-carboxybutyl, etc., and carboxymethyl and 1-carboxyethyl are more preferable.

In the present invention, the polysaccharide having carboxyl groups is preferably a carboxymethylated dextran or pullulan.

When introducing a carboxyalkyl group into polysaccharides, the degree of the introduction thereto is expressed by "degree of substitution" which is defined by the number of carboxyalkyl groups per a sugar residue, i.e. expressed by the following equation.

$$\text{Degree of Substitution} = \frac{\text{Number of carboxyalkyl groups in the molecule}}{\text{Total number of sugar residues in the molecule}}$$

When the carboxyalkyl group is carboxymethyl group, the degree of substitution is occasionally expressed by the degree of carboxymethylation (CM-degree).

When the polysaccharide is pullulan, dextran or mannoglucan, and all of the hydroxy groups thereof are substituted, the degree of substitution thereof is 3, and the preferable degree of substitution is in the range of 0.3 to 0.8.

When the polysaccharide is chitin, and all of the hydroxyl groups thereof are substituted, the degree of substitution thereof is 2, and the preferable degree of substitution is in the range of 0.3 to 0.8.

Besides, it is essential that the polysaccharide of the present invention should have at least one carboxyalkyl group in the molecule except for polysaccharides having originally carboxyl groups. Therefore, polysaccharides having a degree of substitution of 0 should be excluded from the polysaccharide of the present invention.

The polysaccharide having carboxyl groups may be prepared by the method disclosed in WO 94/19376.

The amino acid which intervenes between a camptothecin compound [I] and a polysaccharide having carboxyl groups includes both natural amino acids and synthetic amino acids (including D-amino acid, L-amino acid, a mixture thereof), and also includes either neutral amino acids, basic amino acids or acidic amino acids. Moreover, the amino acid of the present invention may be not only α-amino acids but also β-amino acids, γ-amino acids, ε-amino acids, etc., and includes, for example, glycine, α-alanine, β-alanine, valine, leucine, isoleucine, serine, threonine, cysteine, methionine, aspartic acid, glutamic acid, lysine, arginine, phenylalanine, tyrosine, histidine, tryptophan, proline, hydroxyproline, γ-aminobutyric acid, ε-aminocaproic acid, etc.

The peptide of the present invention includes peptides derived from the above amino acids, or peptides having compounds other than amino acids in the part of the chain thereof. For example, a dicarboxylic acid such as succinic acid, a diamine such as ethylenediamine, or a diol such as ethyleneglycol may exist in the middle of the peptide chain or the terminus of the peptide chain. Besides, the binding site of the peptide chain to the carboxyl groups of the polysaccharide usually starts from the N-terminus of the peptide chain through acid-amide bonds. When a basic amino acid (e.g. lysin) exists in the peptide chain, the binding site of the peptide chain may be reversed by binding an ε-amino group of the basic amino acid with carboxyl groups of a polysaccharide, and binding an α-amino group with the C-terminus of the peptide chain.

Such peptides may be ones composed of two or more amino acids, i.e. ones having two or more peptide chains, more preferably ones having 2 to 5 peptide chains. Suitable examples of the peptide chain are -Gly-Gly-L- or D-Phe-Gly-(SEQ ID NO:3 or 4 respectively), -Gly-Gly-, -Gly-Gly-Gly-, -Gly-Gly-Gly-Gly-(SEQ ID NO:1), -Gly-Gly-Gly-Gly-Gly-(SEQ ID NO:2), -L- or D-Phe-Gly-, -L- or D-Tyr-Gly-, -L- or D-Leu-Gly-, and peptide chains containing these sequences (the N-terminus of these peptides or peptide chains containing these sequences is introduced onto carboxyl groups of a polysaccharide). Among these peptides, -Gly-Gly-L- or D-Phe-Gly-, -Gly-Gly-, -Gly-Gly-Gly-, -Gly-Gly-Gly-Gly-(SEQ ID NO:1), -Gly-Gly-Gly-Gly-Gly-(SEQ ID NO:2), -L- or D-Phe-Gly- and -L- or D-Leu-Gly- are more preferable. Most preferable peptides are -Gly-Gly-L-Phe-Gly-(SEQ ID NO:3), -Gly-Gly-, -Gly-Gly- Gly-, -Gly-Gly-Gly-Gly-(SEQ ID NO:1), and -L- or D-Phe-Gly-.

The camptothecin derivatives of the present invention may usually be prepared by combining the compound [I] with an amino acid or a peptide, followed by reacting the product with a polysaccharide having carboxyl groups.

In the reaction between the compound [I] and an amino acid or a peptide, when $R^6$ of the formula [I] is —$NH_2$ or a piperazino group, the compound [I] is combined with the C-terminal carboxyl group of an amino acid or a peptide through acid-amide bonds. When $R^6$ of the formula [I] is —OH, the compound [I] is combined with the C-terminal carboxyl group of an amino acid or a peptide through ester bonds. In this case, it is preferable to protect other functional groups of an amino acid or a peptide which do not participate in said acid-amide bonds or ester bonds, for example, the N-terminal amino group or other carboxyl groups, are protected in a conventional manner, prior to the reaction of the compound [I] and an amino acid or a peptide. The protecting group may be any protecting groups which are conventionally used for protection of amino acids, and the protecting group of amino group is, for example, t-butoxycarbonyl group, p-methoxybenzyloxycarbonyl group, etc., and the protecting group of carboxyl group is, for example, a lower alkyl group (e.g. t-butyl group), benzyl group, etc.

The production of the above mentioned acid-amide bonds or ester bonds between $R^6$ of the compound [I] and an amino acid or a peptide is carried out by a conventional method, for example, by reacting in the presence of a condensing agent in a suitable solvent. The solvent includes, for example, dimethylformamide, tetrahydrofuran, etc., and the condensing agent includes, for example, dicyclohexylcarbodiimide, 1-(3-dimethylaminopropyl)-3-ethylcarbodiimide hydrochloride, etc.

The camptothecin compound thus prepared by combining the compound [I] with an amino acid or a peptide, after removing the protecting group of an amino group or a carboxyl group therefrom by a conventional method when an amino group or a carboxyl group thereof is protected, is reacted with a polysaccharide having carboxyl groups, to give the desired camptothecin derivatives of the present invention. In this reaction, a part or all of the carboxyl groups of the polysaccharide are combined with the N-terminal amino group of the amino acid or the peptide which is previously bonded to the camptothecin compound [I], through acid-amide bonds.

The reaction of the camptothecin compound which is produced by combining the compound [I] with an amino acid or a peptide, and a polysaccharide having carboxyl groups is carried out by a conventional method, for example, in the presence of a condensing agent in a suitable solvent. The solvent includes, for example, water, ethanol, dimethylformamide, or a mixture thereof, and the condensing agent includes, for example, 1-(3-dimethylaminopropyl)-3-ethylcarbodiimide hydrochloride, 2-ethyloxy-1-ethyloxycarbonyl-1,2-dihydroquinoline, etc.

In the camptothecin derivatives of the present invention, the ratio of the polysaccharide and the camptothecin compound [I] which is an active ingredient may be selected according to the kinds of the polysaccharide to be used, but the content of the camptothecin compound [I] in the camptothecin derivative of the present invention is preferably in the following range.

When the polysaccharide is pullulan, dextran, chitin, mannoglucan or N-acetyl-de-N-sulfuric heparin, it is in the range of 0.1 to 20% by weight, more preferably in the range of 2 to 10% by weight.

When dextran is used as a polysaccharide in the present invention, the average molecular weight of the camptothecin derivative of the present invention is preferably in the range of 30,000 to 500,000, more preferably, in the range of 60,000 to 200,000, determined by the GPC analysis.

The camptothecin derivatives of the present invention thus obtained may be converted into a pharmaceutically acceptable salt thereof, if necessary. The pharmaceutically acceptable salt includes, for example, salts with an alkali metal or an alkaline earth metal (e.g. sodium salt, potassium salt, calcium salt, etc.), or salts with an amino acid (e.g. arginine salt, lysine salt, etc.).

Some of the camptothecin compounds of the formula [I] of the present invention are known compounds, for example, compounds disclosed in Japanese Patent First Publication (Kokai) Nos. 279891/1989, 222048/1993, 87746/1994, 228141/1994 and Japanese Patent First Publication (Kohyo) Nos. 503505/1992, 502017/1993, etc., and may be prepared by conventional methods, such as by the method disclosed in the following Reaction Scheme 1:

Reaction Scheme 1

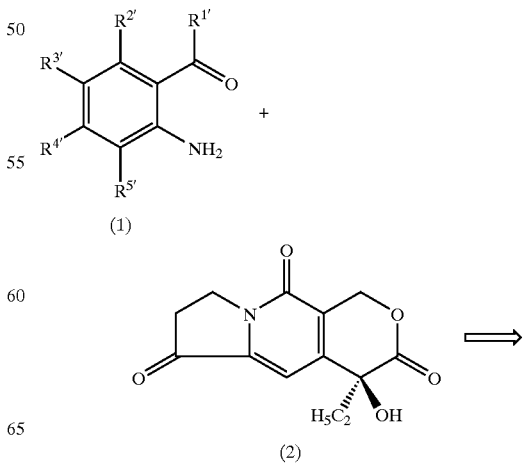

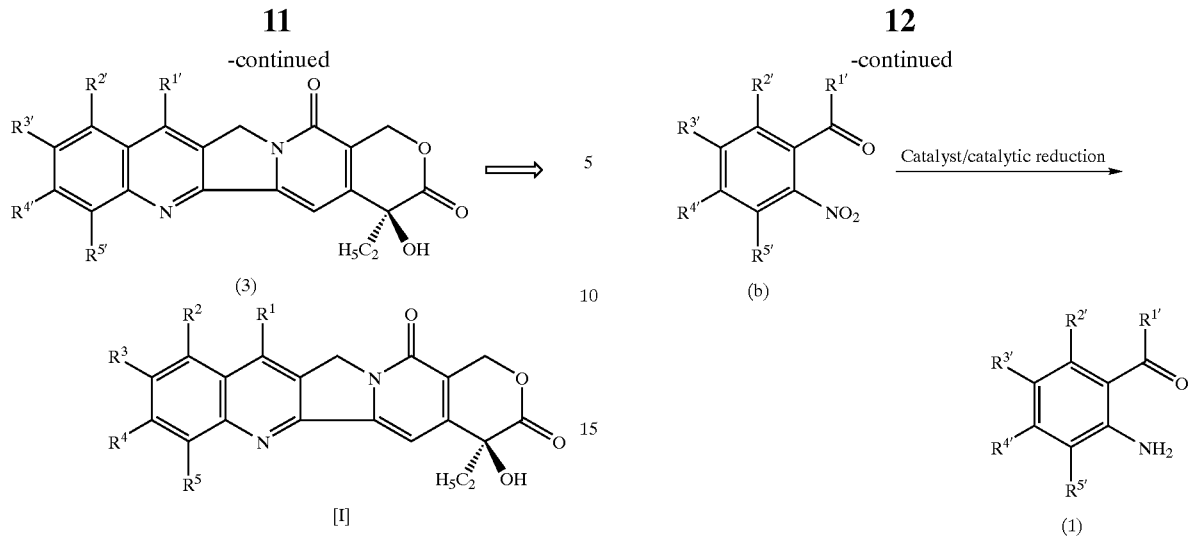

wherein $R^1, R^2, R^3, R^4$ and $R^5$ are the same as defined above, $R^{1'}, R^{2'}, R^{3'}, R^{4'}$ and $R^{5'}$ are the same as $R^1, R^2, R^3, R^4$ and $R^{5'}$ except that an amino group, a piperazino group or a hydroxyl group in the group of the formula: $-X_n\text{-Alk}_m\text{-}R^6$, which is contained in one of $R^{1'}, R^{2'}, R^{3'}, R^{4'}$ and $R^{5'}$ is protected.

That is, the aminocarbonyl compound (1) is condensed with a known pyranoindolidine (2) (cf. EP-0220601-A) by a method known as Friedländer condensation reaction (cf. Organic Reactions, 28, pp. 37–202, John Wiley & Sons, Inc., New York (1982)), followed by removing the protecting groups from the product to give the camptothecin compound [I].

In the above process, a group of the formula: $-X_n\text{-Alk}_m\text{-}R^6$, which is contained in one of $R^{1'}, R^{2'}, R^{3'}, R^{4'}$ and $R^{5'}$ may be introduced after said Friedländer condensation reaction, when m is 1, and n is 1.

That is, in the process of the above Reaction Scheme 1, a compound of the formula (1) wherein a corresponding group to a group of the formula: $-X_n\text{-Alk}_m\text{-}R^6$ is a hydroxyl group (—OH) or an amino group (—NH$_2$) is used, and condensed with the compound (2) by Friedländer condensation reaction, and the resulting condensed product is reacted with a protected aminoalkanol or hydroxyalkanol represented by the formula: $R^{6'}\text{-Alk}_m\text{-OH}$ ($R^{6'}$ is a protected amino group, a protected piperazino group, or a protected hydroxy group, and Alk and m are the same as defined above) or a reactive derivative thereof (e.g. a protected aminoalkyl halide, a protected hydroxyalkyl halide), followed by removing the protecting groups therefrom to give the desired camptothecin compound [I].

The starting aminocarbonyl compound (1) may be prepared by the following Reaction Scheme 2:

Reaction Scheme 2

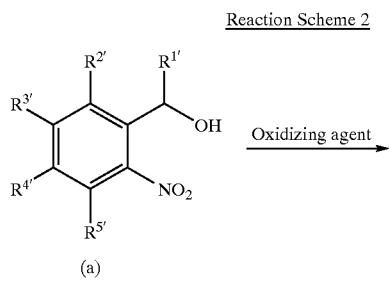

(a)

wherein $R^1$, $R^2$, $R^{3'}$, $R^4$ and $R^{5'}$ are the same as defined above.

The hydroxyl compound (a) is treated with an oxidizing agent such as pyridinium dichromate to give a ketone compound (b), which is further subjected to catalytic reduction in the presence of a suitable catalyst such as palladium-carbon to give the compound (1).

When both m and n are 1, the group of the formula: $-X_n\text{-Alk}_m\text{-}R^6$, which is contained in one of $R^{1'}, R^{2'}, R^{3'}, R^{4'}$ and $R^{5'}$, may be introduced into the compound (a) by reacting a compound of the formula (a) wherein a corresponding group to a group of the formula: $-X_n\text{-Alk}_m\text{-}R^6$ is a hydroxyl group (—OH) or an amino group (—NH$_2$) with a compound of the formula: HO-Alk-$R^6$ (Alk and $R^6$ are the same as defined above) or a reactive derivative thereof (e.g. a substituted alkyl halide).

The camptothecin derivatives of the present invention and a pharmaceutically acceptable salt thereof show excellent antitumor activities against various tumors, especially they show excellent therapeutic effects on solid tumors such as pulmonary cancer, uterine cancer, ovarian cancer, breast cancer, gastrointestinal cancer (large bowel cancer, gastric cancer, etc.).

The camptothecin derivatives of the present invention and a pharmaceutically acceptable salt thereof are preferably administered parenterally (e.g. intravascular injection), and are usually used in the form of a liquid preparation (e.g. solution, suspension, emulsion, etc.).

The dosage of the camptothecin derivatives of the present invention varies according to the administration method, ages, weights or conditions of the patients, but it is usually in the range of 0.02–50 mg/kg/day, more preferably in the range of 0.1–10 mg/kg/day, converted into the dose of the camptothecin compound [I] (when $R^6$ is —NH$_2$, a hydrochloride of the camptothecin compound [I], and when $R^6$ is a group of the formula:

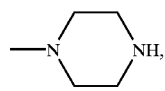

a hydrochloride or dihydrochloride of the camptothecin compound [I]).

The camptothecin derivatives of the present invention and a process for preparing thereof are illustrated in more detail by the following Examples, but should not be construed to be limited thereto.

EXAMPLE 1

Preparation of the camptothecin derivative of the following formula (where -Gly-Gly-L-Phe-Gly- is SEQ ID NO: 3):

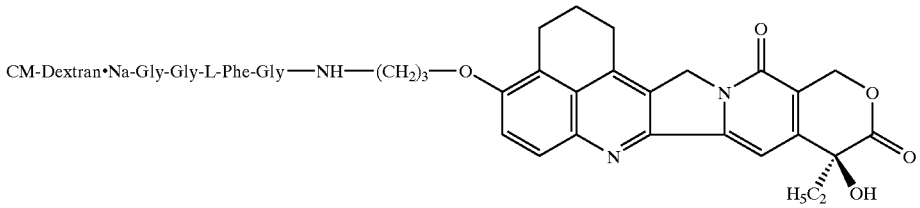

[CM-Dextran Na: carboxymethyldextran sodium salt]

(1) Preparation of 3-(t-butoxycarbonylamino)propanol

3-Aminopropanol (6.0 g) is dissolved in methylene chloride (50 ml), and thereto is added dropwise with stirring di-t-butyl dicarbonate (18.3 g) under ice-cooling. The mixture is stirred at room temperature for 12 hours, and concentrated, and the residue is purified by silica gel column chromatography to give the title compound (13.98 g) as a colorless oil.

Yield: 99.9%
IR (Neat): $v_{max}^{cm-1}$=3380, 1790
Mass: m/z=176 ([M+H]$^+$)
NMR (300 MHz, CDCl$_3$): $\delta^{TMS}$=1.45 (9H, s), 1.62–1.72 (2H, m), 3.0 (1H, brs), 3.29 (2H, dd, J=12 Hz, 6 Hz), 3.66 (2H, dd, J=12 Hz, 6 Hz), 4.80 (1H, brs)

(2) Preparation of 3-(t-butoxycarbonylamino)propyl tosylate 3-(t-Butoxycarbonylamino)propanol (10.0 g) is dissolved in methylene chloride (100 ml), and thereto are added with stirring triethylamine (8.66 g) and tosyl chloride (16.3 g) under ice-cooling, and the reaction mixture is stirred at room temperature overnight. The reaction mixture is concentrated, and the residue is dissolved in a mixture of water and ethyl acetate. The organic layer is separated, washed with a saturated sodium chloride solution, dried over sodium sulfate, and concentrated under reduced pressure. The residue is purified by silica gel column chromatography to give the title compound (15.37 g) as a pale yellow oil.

Yield: 82%
IR (Neat): $v_{max}^{cm-1}$=3400, 3340, 1700
Mass: m/z=352 ([M+Na]$^+$)
NMR (300 MHz, CDCl$_3$): $\delta^{TMS}$=1.42 (9H, s), 1.78–1.90 (2H, m), 2.45 (3H, s), 3.11–3.22 (2H, m), 4.09 (2H, t, J=6 Hz), 4.5–4.65 (1H, m), 7.36 (2H, d, J=8 Hz), 7.77–7.83 (2H, m)

(3) preparation of 5-[3'-(t-butoxycarbonylamino) propyloxy]-1-hydroxy-8-nitro-1,2,3,4-tetrahydronaphthalene 1,5-Dihydroxy-8-nitro-1,2,3,4-tetrahydronaphthalene (2.0 g) (J. Med. Chem., 1973, 16 (3), 254) is dissolved in dry DMF (80 ml), and thereto are added potassium carbonate (2 equivalents), sodium iodide (1.4 equivalent) and 3-(t-butoxycarbonylamino)propyl tosylate (1.4 equivalent). The reaction mixture is stirred at 50° C. for 24 hours, and thereto is added ethyl acetate. The mixture is washed with a saturated aqueous sodium chloride solution, and dried over sodium sulfate. The residue is purified by silica gel column chromatography to give the title compound (3.05 g) as a pale yellow amorphous powder.

Yield: 87%
IR (Neat): $v_{max}^{cm-1}$=3360, 1695
Mass: m/z=384 ([M+NH$_4$]$^+$)

NMR (300 MHz, CDCl$_3$): $\delta^{TMS}$=1.36 (9H, s), 1.57–1.90 (6H, m), 2.52–2.71 (2H, m), 3.11 (2H, q, J=6 Hz), 4.07 (2H, t, =6 Hz), 5.12–5.17 (2H, m), 6.89 (1H, t, J=5.5 Hz), 6.96 (1H, d, J=9 Hz), 7.68 (1H, d, J=9 Hz)

(4) Preparation of 5-[3'-(t-butoxycarbonylamino) propyloxy]-8-nitro-1,2,3,4-tetrahydronaphthalen-1-one 5-[3'-(t-Butoxycarbonylamino)propyloxy]-1-hydroxy-8-nitro-1,2,3,4-tetrahydronaphthalene (2.46 g) is dissolved in dry methylene chloride (110 ml), and thereto are added molecular sieves 3A (6.73 g) and pyridinium dichlorochromate (1.5 equivalent), and the mixture is refluxed. After the reaction is completed, the mixture is diluted with ether, and the insoluble materials are removed by filtration through a pad of Celite. The filtrate is concentrated, and the residue is purified by silica gel column chromatography to give the title compound (1.87 g) as a colorless powder.

M.p. 76–77° C.
Yield: 76%
IR (Melt): $v_{max}^{cm-1}$=3550, 1700
Mass: m/z=382 ([M+NH$_4$]$^+$)
NMR (300 MHz, CDCl$_3$): $\delta^{TMS}$=1.44 (9H, s), 2.02–2.20 (4H, m), 2.68–2.73 (2H, m), 2.92 (2H, t, J=6 Hz), 3.36 (2H, q, J=6.5 Hz), 4.12 (2H, t, J=6 Hz), 4.78 (1H, brs), 6.95 (1H, d, J=9 Hz), 7.39 (1H, d, J=9 Hz)

(5) Preparation of 8-amino-5-[3'-(t-butoxycarbonylamino) propyloxy]-1,2,3,4-tetrahydronaphthalen-1-one 5-[3'-(t-Butoxycarbonylamino)propyloxy]-8-nitro-1,2,3,4-tetrahydronaphthalen-1-one (3.55 g) is dissolved in ethanol (160 ml), and thereto is added 10% palladium-carbon (420 mg). The mixture is stirred under hydrogen atmosphere for 1.5 hour, and the catalyst is removed by filtration. The filtrate is concentrated, and the residue is purified by silica gel column chromatography to give the title compound (3.56 g) as a yellow oil.

M.p.: 112–115° C.
Yield: 83%
IR (Nujol): $v_{max}^{cm-1}$=3440, 3340, 1700, 1650
Mass: m/z=335 ([M+H]$^+$)
NMR (300 MHz, CDCl$_3$): $\delta^{TMS}$=1.45 (9H, s), 1.92–2.67 (4H, m), 2.61 (2H, t, J=6 Hz), 2.87 (2H, t, J=6 Hz), 3.35 (2H, q, J=6.5 Hz), 3.94 (2H, t, J–6 Hz), 4.85 (1H, brs), 6.10 (2H ,brs), 6.48 (1H, d, J=9 Hz), 6.94 (1H, d, J=9 Hz)

(6) Preparation of 10-[3'-(t-butoxycarbonylamino) propyloxy]-7,9-trimethylene-(20S)-camptothecin 8-Amino-5-[3'-(t-butoxycarbonylamino)propyloxy]-1,2,3,4-tetrahydronaphthalen-1-one (2.03 g) is dissolved in ethanol (85 ml), and thereto are added (4S)-7,8-dihydro-4-ethyl-4-hydroxy-1H-pyrano[3,4-f]indolidine-3,6,10(4H)-trione (800 mg) and p-toluenesulfonic acid (58 mg), and the mixture is refluxed for 17 hours. After the reaction is completed, the mixture is concentrated under reduced pressure to remove the solvent, and the resulting residue is purified by silica gel column chromatography to give the title compound (850 mg) as a pale yellow powder.

M.p.: 225–227° C. (decomposed)
Yield: 50%
IR (Nujol): $v_{max}^{cm-1}$=3440, 3325, 1750, 1740, 1655, 1620
Mass: m/z=562 ([M+H]$^+$)
NMR (300 MHz, CDCl$_3$): $\delta^{TMS}$=1.03 (3H, t, J=7.5 Hz), 1.45 (9H, s), 1.82–2.18 (6H, m), 3.06–3.13 (4H, m), 3.41 (2H, q, J=6 Hz), 3.79 (1H, s), 4.24 (2H, t, J=6 Hz), 4.9 (1H, br), 5.16 (2H, s), 5.30 (1H, d, J=16 Hz), 5.75 (1H, d, J=16 Hz), 7.51 (1H, d, J=9 Hz), 7.61 (1H, s), 8.06 (1H, d, J=9 Hz)

(7) Preparation of 10-(3'-aminopropyloxy)-7,9-trimethylene-(20S)-camptothecin hydrochloride 10-[3'-(t-Butoxycarbonylamino)propyloxy]-7,9-trimethylene-(20S)-camptothecin (836 mg) is suspended in dioxane (30 ml), and thereto is added dropwise with stirring a 18% hydrochloric acid in dioxane (15 ml) under ice-cooling. The reaction mixture is stirred at room temperature, and after the reaction is completed, isopropyl ether is added to the reaction mixture, and stirred. The precipitated powder is collected by filtration, washed with ether, and dried under reduced pressure. The yellow powder thus obtained is dissolved in water, and lyophilized to give the title compound (620 mg) as a yellow powder.

M.p.: >194° C. (decomposed)
Yield: 84%
IR (Nujol): $v_{max}^{-1}$=1740, 1655
Mass: m/z=462 ([M–Cl]$^+$)
NMR (300 MHz, d$_6$-DMSO): $\delta^{TMS}$=0.88 (3H, t, J=7.5 Hz), 1.81–1.94 (2H, m), 1.97–2.15 (4H, m), 3.01–3.14 (6H, m), 4.28 (2H, t, J=6 Hz), 5.23 (2H, s), 5.43 (2H, s), 7.28 (1H, s), 7.71 (1H, d, J=9.5 Hz), 7.95–8.08 (3H, brs), 8.03 (1H, d, J=9.5 Hz)

(8) Preparation of 10-[3'-(t-butoxycarbonylglycylglycyl-L-phenylalanyl-glycylamino)propyloxy]-7,9-trimethylene-(20S)-camptothecin 10-(3'-Aminopropyloxy)-7,9-tri methylene-(20S)-camptothecin hydrochloride (158 mg) and diisopropylethylamine (49 mg) are dissolved with stirring in DMF (5 ml), and thereto is added a solution of t-butoxycarbonyl-glycylglycyl-L-phenylalanylglycine (278 mg) and N-hydroxysuccinimide (143 mg) in dry DMF (8 ml), and further added thereto with stirring 1-(3-dimethylaminopropyl)-3-ethylcarbodiimide hydrochloride (183 mg) under ice-cooling. The mixture is stirred at room temperature for 16 hours. After the reaction is completed, the mixture is concentrated under reduced pressure to remove the solvent, and the resulting residue is purified by silica gel column chromatography to give the title compound (285 mg) as a pale yellow powder.

Yield: Quantitative
IR (Nujol): $v_{max}^{cm-1}$=3290, 1660
Mass: m/z=880 ([M+H]$^+$)
NMR (300 MHz, CDCl$_3$): $\delta^{TMS}$=1.02 (3H, t, J=7.5 Hz), 1.43 (9H, s), 1.85–1.94 (2H, m), 2.02–2.10 (4H, m), 2.97–3.05 (5H, m), 3.23 (1H, dd, J=14 Hz, 5Hz), 3.49 (2H, q, J=6.5 Hz), 3.60–3.80 (6H, m), 4.20 (1H, t, J=6 Hz), 4.50–4.56 (1H, m), 5.11 (2H, s), 5.29 (1H, d, J=16.5 Hz), 5.71 (1H, d, J=16.5 Hz), 5.85 (1H, brt), 7.08 (1H, m), 7.18–7.27 (5H, m), 7.45 (1H, d, J=7 Hz), 7.52 (1H, d, J=9.5 Hz), 7.58 (1H, s), 7.71 (1H, m), 7.99 (1H, d, J=9.5 Hz)

(9) Preparation of 10-[3'-(glycylglycyl-L-phenylalanylglycylamino)propyloxy]-7,9-trimethylene-(20S)-camptothecin hydrochloride 10-[3'-(t-Butoxycarbonylglycylglycyl-L-phenylalanylglycylamino)propyloxy]-7,9-trimethylene-(20S)-camptothecin (273 mg) is dissolved in dioxane (10 ml), and thereto is added dropwise with stirring 18% hydrochloric acid in dioxane (15 ml) under ice-cooling. The reaction mixture is stirred at room temperature, and after the reaction is completed, to the mixture is added isopropyl ether. The mixture is stirred, and the precipitated powder is collected by filtration, washed with ether, and dried under reduced pressure. The yellow powder thus obtained is dissolved in water, and lyophilized to give the title compound (210 mg) as a yellow powder.

M.p.: >174° C. (decomposed)
Yield: 83%
IR (Nujol): $v_{max}^{cm-1}$=3190, 1745, 1650
Mass: m/z=780 ([M–Cl]$^+$)
NMR (300 MHz, d$_6$-DMSO): $\delta^{TMS}$=0.89 (3H, t, J=7Hz), 1.26–1.32 (2H, m), 1.86–2.04 (6H, m), 2.79 (1H, dd, J=14 Hz, 10 Hz), 2.98–3.05 (5H, m), 3.28–3.36 (2H, m), 3.54–3.88 (6H, m), 4.20 (2H, t, J=6 Hz), 4.45–4.54 (1H, m), 5.19 (2H, s), 5.43 (2H, s), 7.11–7.27 (5H, m), 7.35 (1H, s), 7.71 (1H, t, J=9.5 Hz), 7.97 (1H, t, J=5.5 Hz), 8.03 (1H, d, J=9.5 Hz), 8.19 (3H, br), 8.35 (1H, t, J=6 Hz), 8.43 (1 H, d, J=8 Hz), 8.65 (1H, t, J=5.5 Hz)

The camptothecin compound having an amino group obtained by the above process is condensed with a water soluble high molecular compound having carboxyl groups such as carboxymethyldextran (hereinafter, referred to as CM-dextran) to give the desired camptothecin derivative. The condensation reaction is carried out in the presence of a condensing agent such as a water soluble carbodiimide [1-(3-dimethylaminopropyl)-3-ethylcarbodiimide hydrochloride, 2-ethoxy-1-ethoxycarbonyl-1,2-dihydroquinoline, etc.] in a water or a mixture of water-an organic solvent.

(10) Preparation of the Camptothecin Derivative

CM-Dextran sodium salt (CM-degree; 0.5) (500 mg) is dissolved in water (20 ml), and thereto is added with stirring 10-[3'-(glycyl-glycyl-L-phenylalanyl-glycylamino) propyloxy]-7,9-trimethylene-(20S)-camptothecin hydrochloride (50 mg) at a temperature below 10° C. To the mixture is added 1-(3-dimethylaminoproplyl)-3-ethylcarbodiimide hydrochloride (1.5 g), during which the pH value of the mixture is kept at pH 6.5–7.0 with 0.1N hydrochloric acid. The mixture is stirred at a temperature below 10° C. for two hours, and the pH value thereof is adjusted to pH 9 with 0.1N sodium hydroxide. The reaction mixture is purified by ion-exchange column chromatography (AGMP-50, Na-type, 30 ml, manufactured by Bio-Rad, Laboratories, Inc.). The fractions containing the desired compound are combined (30 ml), and thereto is added a 3M aqueous sodium chloride solution (1.2 ml), and the mixture is poured into ethanol (150 ml). The precipitates are collected by centrifugation, and water (20 ml) is added to the precipitate, and then the mixture is filtered. To the filtrate is added a 3M aqueous sodium chloride solution (0.4 ml), and the mixture is added with stirring to ethanol (80 ml). The precipitates are collected by centrifugation, washed with the solvent, and dried under reduced pressure to give the desired camptothecin derivative (415 mg). The content of 10-(3'-aminopropyloxy)-7,9-trimethylene-(20S)-camptothecin hydrochloride (the compound of Example 1-(7)) in the desired camptothecin derivative is 4.4% which is calculated on the basis of the absorbance at 380 nm. According to the analysis by gel permeation chromatography (GPC), the average molecular weight of the desired camptothecin derivative is 160,000, and the degree of distribution (Mw/Mn) is 1.57.

Conditions for GPC analysis: G4000SWXL (manufactured by Toso, Ltd), 0.2M phosphate buffer (pH 7.0)

EXAMPLE 2

Preparation of the camptothecin derivative of the following formula (where-Gly-Gly-L-Phe-Gly- is SEQ ID NO: 3):

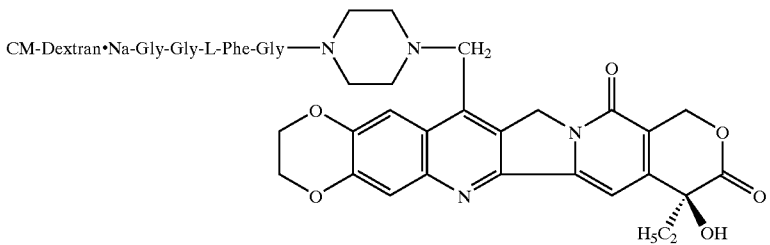

(1) Preparation of 7-(4'-(t-butoxycarbonylglycylglyclyl-L-phenylalanylglycyl)piperazino)methyl-10,11-ethylenedioxy-(20S)-camptothecin The title compound (518 mg) is obtained in the same manner as in Example 1-(8) as a yellow powder from 7-piperazinomethyl-10,11-ethylenedioxy-(20S)-camptothecin hydrochloride (450 mg) and t-butoxycarbonyl-glycyl-glycyl-L-phenylalanylglycine (2 equivalents).

Yield: 74%
IR (Nujol): $v_{max}^{cm-1}$=3280, 1750, 1655
Mass: m/z=923 ([M+H]$^+$)
NMR (300 MHz, d$_6$-DMSO): $\delta^{TMS}$=0.89 (3H, t, J=7.5 Hz), 1.37 (9H, s), 1.85–2.1 (2H, m), 2.3–2.6 (4H, m), 2.75 (1H, dd, J=14 Hz, 10 Hz), 3.05 (1H, dd J=14 Hz, 4.5 Hz), 3.3–3.6 (6H, m), 3.58 (1H, dd, J=21 Hz, 5.5 Hz), 3.74 (1H, dd, J=17 Hz, 5.5 Hz), 3.9–4.1 (4H, m), 4.44 (4H, s), 4.58 (1H, m), 5.24 (2H, s), 5.42 (2H, s), 6.50 (1H, s), 6.97 (1H, t, J=6 Hz), 7.1–7.3 (6H, m), 7.55 (1H, s,) 7.77 (1H, s), 7.8–7.9 (1H, br), 8.05–8.2 (2H, m)

(2) Preparation of 7-(4'-(glycylglycyl-L-phenylalanylglycyl)piperazino)methyl-10,11-ethylenedioxy-(20S)-camptothecin hydrochloride The title compound (409 mg) is obtained in the same manner as in Example 1-(9) as a yellow powder from 7-(4'-(t-butoxycarbonylglycylglycyl-L-phenylalanylglycyl)piperazino)methyl-10,11-ethylenedioxy-(20S)-camptothecin (478 mg).

M.p. 237–239° C. (decomposed)
IR (Nujol): $v_{max}^{cm-1}$=3250, 1745, 1655
Mass: m/z=823 ([M–Cl]$^+$)
NMR (300 MHz, d$_6$-DMSO): $\delta^{TMS}$=0.88 (3H, t, J=7 Hz), 1.8–1.99 (2H, m), 2.79 (1H, dd, J=14 Hz, 10 Hz), 3.07 (1H, dd, J=14 Hz, 4 Hz), 3.1–4.3 (16H, m,) 4.47 (4H, s), 4.55–4.70 (1H, m), 5.44 (2H, s), 5.67 (2H, s), 7.15–7.32 (6H, m), 7.65 (1H, s), 8.05 (1H, s), 8.05–8.20 (3H, br), 8.29 (1H, br), 8.39 (1H, d, J=8.5 Hz), 8.57 (1H, t, J=5.5 Hz)

(3) Preparation of the Camptothecin Derivative

CM-Dextran sodium salt (CM-degree; 0.5) (1.2 g) and 7-(4'-(glycyl-glycyl-L-phenylalanylglycyl)piperazino)methyl-10,11-ethylenedioxy-(20S)-camptothecin hydrochloride (168 mg) are treated in the same manner as in Example 1-(10) to give the desired camptothecin derivative (798 mg) as a pale yellow powder. The content of 7-piperazinomethyl-10,11-ethylenedioxy-(20S)-camptothecin hydrochloride in the desired camptothecin derivative is 1.1% which is calculated on the basis of the absorbance at 380 nm. According to the analysis by gel permeation chromatography (GPC), the average molecular weight of the desired camptothecin derivative is 169,000, and the degree of distribution (Mw/Mn) is 1.32.

Conditions for GPC analysis: G4000SWXL (manufactured by Toso, Ltd), 0.2M phosphate buffer (pH 7.0)

EXAMPLE 3

Preparation of the camptothecin derivative of the following formula (where -Gly-Gly-L-Gly- is SEQ ID NO: 3):

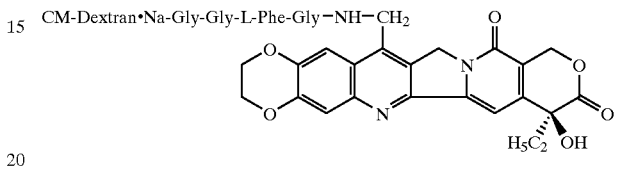

(1) Preparation of 7-N-(t-butoxycarbonylglycylglyclyl-L-phenylalanyl-glycyl)aminomethyl-10,11-ethylenedioxy-(20S)-camptothecin The title compound (232 mg) is obtained in the same manner as in Example 1-(8) as a yellow powder from 7-aminomethyl-10,11-ethylenedioxy-(20S)-camptothecin hydrochloride (222 mg) and t-butoxycarbonyl-glycyl-glycyl-L-phenylalanylglycine (2 equivalents).

Yield: 58%
IR (Nujol): $v_{max}^{cm-1}$=3285, 1750, 1650
Mass: m/z=854 ([M+H]$^+$)
NMR (300 MHz, d$_6$-DMSO): $\delta^{TMS}$=0.88 (3H, t, J=7.5 Hz), 1.35 (9H, s), 1.78–1.94 (2H, m), 2.74 (1H, dd, J=14 Hz, 10 Hz), 2.99 (1H, dd, J=14 Hz, 4.5 Hz), 3.4–3.8 (4H, m), 4.34–4.50 (1H, m), 4.42 (4H, s), 4.66–4.82 (2H, m), 5.42 (4H, brs), 6.50 (1H, s), 6.98 (1H, t, J=6 Hz), 7.12–7.28 (5H, m), 7.26 (1H, s), 7.56 (1H, s), 7.80 (1H, s), 7.91 (1H, br), 8.14 (1H, d, J=7.5 Hz), 8.32 (2H, t, J=7.5 Hz), 8.58 (1H, m)

(2) Preparation of 7-N-(glycylglycyl-L-phenylalanylglycyl)aminomethyl-10,11-ethylenedioxy-(20S)-camptothecin hydrochloride The title compound (164 mg) is obtained in the same manner as in Example 1-(9) as a yellow powder from 7-N-(t-butoxycarbonylglycylglycyl-L-phenylalanylglycyl)aminomethyl-10,11-ethylenedioxy-(20S)-camptothecin (203 mg).

M.p. >211° C. (decomposed)
IR (Nujol): $v_{max}^{cm-1}$=3220, 1745, 1655
Mass: m/z=754 ([M–Cl]$^+$)
NMR (300 MHz, d$_6$-DMSO): $\delta^{TMS}$=0.88 (3H, t, J=7 Hz), 1.80–1.93 (2H, m), 2.77 (1H, dd, J=14 Hz, 10 Hz), 3.00 (1H, dd, J=14 Hz, 4 Hz), 3.6–4.55 (7H, m), 4.42 (4H, s), 4.65–4.85 (2H, m), 5.42 (2H, s), 5.45 (2H, s), 7.13–7.26 (5H, m), 7.27 (1H, s), 7.57 (1H, s), 7.83 (1H, s), 8.03–8.16 (3H, br), 8.34–8.40 (2H, m), 8.54 (1H, br), 8.73 (2H, br)

(3) Preparation of the Camptothecin Derivative

CM-Dextran sodium salt (CM-degree; 0.5) (772 m) is dissolved in water (50 ml), and thereto is added DMF (25 ml). The mixture is stirred under ice-cooling, and thereto are added 7-N-(glycylglycyl-L-phenylalanylglycyl)aminomethyl-10,11-ethylenedioxy-(20S)-camptothecin hydrochloride (106 mg) and 2-ethoxy-1-ethoxycarbonyl-1,2-dihydroquinone (1.57 g). The mixture is reacted overnight, and added into ethanol (450 ml) to give the precipitates, which are further treated in the same manner as in Example 1-(10) to give the desired camptothecin derivative (545 mg) as a pale yellow powder. The content of 7-aminomethyl-10,11 -ethylenedioxy-(20S)-camptothecin hydrochloride in the desired camptothecin derivative is 5.5% which is calculated on the basis of the absorbance at 375 nm. According to the analysis by gel permeation chromatography (GPC), the average molecular weight of the desired camptothecin derivative is 165,000, and the degree of distribution (Mw/Mn) is 1.40.

Conditions for GPC analysis: G4000SWXL (manufactured by Toso, Ltd), 0.2M phosphate buffer (pH 7.0)

EXAMPLE 4

Preparation of 10-(3'-aminopropyloxy)-(20S)-camptothecin hydrochloride (1) Preparation of 5-[3'-(t-butoxycarbonylamino) propyloxy]-2-nitrobenzaldehyde dimethyl acetal 5-Hydroxy-2-nitrobenzaldehyde dimethyl acetal (3.0 g) is dissolved in dry dimethylformamide (50 ml), and thereto are added sodium iodide (3.15 g), potassium carbonate (1.93 g) and 3-(t-butoxycarbonylamino)propyl tosylate (6.95 g). The mixture is stirred at 50° C. for three hours, and cooled to room temperature. The mixture is extracted with ethyl acetate, and the extract is washed with a saturated aqueous sodium chloride solution, and dried over sodium sulfate. The resultant is concentrated under reduced pressure to remove the solvent, and the residue is purified by silica gel column chromatography to give the title compound (5.22 g) as a pale yellow oil.

Yield: Quantitative

IR (Neat): $v_{max}^{cm-1}$=3360, 1710

Mass: m/z=393 ([M+Na]$^+$)

NMR (300 MHz, CDCl$_3$): $\delta^{TMS}$=1.44 (9H, s), 2.02 (2H, quint., J=6 Hz), 3.33 (2H, dd, J=13 Hz, 6 Hz), 3.44 (6H, s), 4.11 (2H, t, J=6 Hz), 4.7 (1H, brs), 6.01 (1H, s), 6.90 (1H, dd, J=9 Hz, 3 Hz), 7.29 (1H, d, J=3 Hz), 7.97 (1H, d, J=9 Hz)

(2) Preparation of 10-[3'-(t-butoxycarbonylamino) propyloxy]-(20S)-campthothecin 5-[3'-(t-Butoxycarbonylamino)propyloxy]-2-nitrobenzaldehyde dimethyl acetal (1270 mg) is dissolved in ethanol (20 ml), and thereto is added 10% palladium-carbon (120 mg), and the mixture is stirred under hydrogen atmosphere for 1.5 hour. The catalyst is removed by filtration, and to the filtrate are added (4S)-7,8-dihydro-4-ethyl-4-hydroxy-1H-pyrano[3,4-f]-indolidine-3,6,10(4H)-trione (300 mg) and p-toluenesulfonic acid (22 mg), and the mixture is stirred at room temperature overnight. The mixture is concentrated under reduced pressure to remove the solvent, and the residue is purified by silica gel column chromatography to give the title compound (204 mg) as a pale yellow powder.

M.p. 223–224° C. (decomposed)

Yield: 34%

IR (Nujol): $v_{max}^{cm-1}$=3360, 1750, 1690

Mass: m/z=522 ([M+H]$^+$)

NMR (300 MHz, CDCl$_3$): $\delta^{TMS}$=1.03 (3H, t, J=7.5 Hz), 1.46 (9H, s), 1.8–2.0 (2H, m), 2.08 (1H, dd, J=12.5 Hz, 6.5 Hz), 2.10 (1H, dd, J=12.5 Hz, 6 Hz), 3.40 (2H, q, J=6.5 Hz), 4.18 (2H, t, J=6 Hz), 4.82 (1H, brs), 5.24 (2H, s), 5.29 (1H, d, J=16 Hz), 5.73 (1H, d, J=16 Hz), 7.12 (1H, d, J=3 Hz), 7.43 (1H, dd, J=9 Hz, 3 Hz), 7.61 (1H, s), 8.09 (1H, d, J=9 Hz), 8.20 (1H, d, J=9 Hz)

(3) Preparation of 10-(3'-aminopropyloxy)-(20S)-camptothecin hydrochloride

10-[3'-(t-Butoxycarbonylamino)propyloxy]-(20S)-camptothecin (352 mg) is dissolved in dry dioxane-ethanol (7 ml-1 ml), and to the mixture is added with stirring 19% hydrochloric acid in dioxane (5 ml) under ice-cooling. The reaction mixture is stirred at room temperature, and thereto is added isopropyl ether (10 ml). The precipitated powder is collected by filtration, and washed to give the title compound (339 mg) as a yellow powder.

M.p. 214–218° C. (decomposed)

IR (Nujol): $v_{max}^{cm-1}$=3470, 3280, 1745

Mass: m/z=422 ([M–Cl]$^+$)

NMR (300 MHz, d$_6$-DMSO): $\delta^{TMS}$=0.89 (3H, t, J=7.5 Hz), 1.80–1.95. (2H, m), 2.10–2.22 (2H, m), 2.96–3.10 (2H, m), 4.27 (2H, t, J=6 Hz), 5.25 (2H, s), 5.42 (2H, s), 7.29 (1H, s), 7.49–7.55 (2H, m), 8.08 (1H, d, J=10 Hz), 8.19 (3H, brs), 8.54(1H, s)

EXAMPLE 5

Preparation of 10-[3'-(glycyl-glycyl-L-phenylalanyl-glycylamino)propyloxy]-(20S)-camptothecin hydrochloride (1) Preparation of 10-[3'-(t-butoxycarbonyl-glycyl-glycyl-L-phenylalanyl-glycylamino)propyloxy]-(20S)-camptothecin 10-(3'-Aminopropyloxy)-(20S)-camptothecin hydrochloride (325 mg) is dissolved in dry dimethylformamide (10 ml), and thereto are added with stirring N-hydroxysuccinimide (4 equivalents), diisopropylethylamine (2 equivalents), N-t-butoxycarbonyl-glycyl-glycyl-L-phenylalanylglycine (2 equivalents) and 1-(3-dimethylaminopropyl)-3-ethylcarbodiimide hydrochloride (4 equivalents) under ice-cooling. The reaction mixture is stirred at room temperature overnight, and concentrated under reduced pressure to remove the solvent. The residue is purified by silica gel column chromatography to quantitatively give the title compound (597 mg) as a yellow powder.

IR (Nujol): $v_{max}^{cm-1}$=3280, 1750, 1660

Mass: m/z=840 ([M+H]$^+$)

NMR (300 MHz, d$_6$-DMSO): $\delta^{TMS}$=0.88 (3H, t, J=7 Hz), 1.36 (9H, s), 1.8–2.04 (4H, m), 2.72–2.84 (1H, m), 3.00–3.12 (1H, m), 3.24–3.36 (2H, m), 3.50–3.80 (6H, m), 4.18 (2H, t, J=6 Hz), 4.44–4.54 (1H, m), 5.24 (2H, s), 5.42 (2H, s), 6.50 (1H, s), 6.99 (1H, t, J=6 Hz), 7.12–7.27 (5H, m), 7.28 (1H, s), 7.48–7.55 (1H, m), 7.50 (1H, s), 7.88–7.96 (1H, m), 8.07 (1H, d, J=9 Hz), 8.12–8.36 (2H, m), 8.51 (1H, s)

(2) Preparation of 10-[3'-(glycyl-glycyl-L-phenylalanyl-glycylamino)propyloxy]-(20S)-camptothecin hydrochloride 10-[3'-(t-Butoxycarbonyl-glycyl-glycyl-L-phenylalanyl-glycylamino)propyloxy]-(20S)-camptothecin (580 mg) is treated in the same manner as in Example 4-(3) to give the title compound (438 mg) as a yellow powder.

Yield: 82%

M.p. 194–199° C. (decomposed)

IR (Nujol): $v_{max}^{cm-1}$=3190, 1745, 1650

Mass: m/z=740 ([M–Cl]$^+$)

NMR (300 MHz, d$_6$-DMSO): $\delta^{TMS}$=0.88 (3H, t, J=7 Hz), 1.80–2.03 (4H, m), 2.79 (1H, dd, J=14 Hz,10 Hz), 3.05 (1H, dd, J=14 Hz, 5 Hz), 3.2–3.5 (2H, m), 3.52–3.62 (2H, m), 3.62–3.83 (4H, m), 4.19 (2H, t, J=6 Hz), 4.48–4.58 (1H, m), 5.25 (2H, s), 5.42 (2H, s), 6.5 (1H, brs), 7.13–7.26 (5H, m), 7.28 (1H, s), 7.49–7.55 (1H, m), 7.50 (1H, s, J=9.5 Hz), 7.93 (1H, t, J=6 Hz), 8.0–8.14 (4H, m). 8.32–8.41 (2H, m), 8.51 (1H, s), 8.56 (1H, t, J=5.5 Hz)

EXAMPLE 6

Preparation of the camptothecin derivative of the following formula (where -Gly-Gly-L-Phe-Gly- is SEQ ID NO: 3):

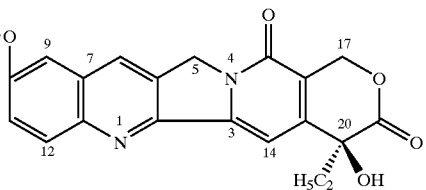

CM-Dextran sodium salt (CM-degree; 0.5) (513 mg) is dissolved in water (50 ml), and thereto are added with stirring 10-[3'-(glycyl-glycyl-L-phenylalanyl-glycylamino) propyloxy]-(20S)-camptothecin hydrochloride (77 mg) and 1-(3-dimethylaminopropyl)-3-ethylcarbodiimide hydrochloride (1.54 g), during which the butch temperature is kept at a temperature below 10° C. The mixture is stirred for two hours at a butch temperature of below 10° C., during which the pH value of the mixture is kept at pH 6.0–6.5 with 0.2N hydrochloric acid. The reaction mixture is purified by ion-exchange column chromatography (AGMP-50, Na-type, 30 ml, manufactured by Bio-Rad, Laboratories, Inc.). The fractions containing the desired compound are combined, filtered, and to the filtrate is added ethanol. The precipitates are collected by centrifugation, washed, and dried under reduced pressure to give a pale yellow powdery complex (492 mg). The content of 10-(3'-aminopropyloxy)-(20S)-camptothecin hydrochloride in the desired camptothecin derivative is 2.8% which is calculated on the basis of the absorbance at 380 nm. According to the analysis by gel permeation chromatography (GPC), the average molecular weight of the desired camptothecin derivative is 179,000, and the degree of distribution (Mw/Mn) is 1.42.

Conditions for GPC analysis: G4000SWXL (manufactured by Toso, Ltd), 0.2M phosphate buffer (pH 7.0)

EXAMPLE 7

Preparation of the camptothecin derivative of the following formula (where -Gly-Gly-L-Phe-Gly- is SEQ ID NO: 3):

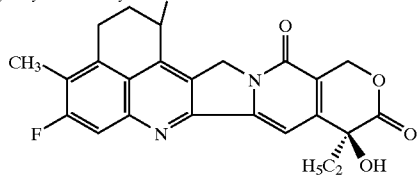

(1) Preparation of (9S)-1-(t-butoxycarbonylglycylglyclyl-L-phenylalanyl-glycylamino)-9-ethyl-5-fluoro-2,3-dihydro-9-hydroxy-4-methyl-1H,12H-benzo[de]pyrano[3',4':4,6,7]indolidino[1,2-b]quinoline-10,13[9H,15H]-dione The title compound (247 mg) is obtained in the same manner as in Example 1-(8) as a pale yellow amorphous solid from (9S)-1-amino-9-ethyl-5-fluoro-2,3-dihydro-9-hydroxy-4-methyl-1H,12H-benzo[de]pyrano[3',4':6,7]-indolidino[1,2-b]quinoline-10,13[9H,15H]-dione hydrochloride (166 mg) and t-butoxycarbonylglycylglyclyl-L-phenylalanylglycine (2 equivalents).

Yield: 82%

IR (Nujol): $v_{max}^{cm-1}$=3290, 1710, 1655

Mass: m/z=854 ([M+H]$^+$)

NMR (300 MHz, d$_6$-DMSO): $\delta^{TMS}$=0.87 (3H, t, J=7 Hz), 1.37 (9H, s), 1.8–1.95 (2H, m), 2.05–2.3 (1H, m), 2.42 (3H, s), 2.5–2.85 (2H, m), 2.9–3.1 (1H, m), 3.15–3.4 (2H, m), 3.5–3.8 (6H, m), 4.4–4.55 (1H, m), 5.26 (2H, s), 5.42 (2H, s), 5.55–5.65 (1H, m), 6.53 (1H, s), 6.99 (1H, t, J=5 Hz), 7.1–7.3 (5H, m), 7.32 (1H, s), 7.81 (1H, d, J=11 Hz), 7.8–7.95 (1H, m), 8.1–8.2 (1H, m), 8.3–8.4 (1H, m), 8.4–8.5 (1H, m)

(2) Preparation of (9S)-1-(glycyl-glycyl-L-phenylalanylglycylamino)-9-ethyl-5-fluoro-2,3-dihydro-9-hydroxy-4-methyl-1H,12H-benzo[de]pyrano[3',4':6,7]indolidino[1,2-b]quinoline-10,13[9H,15H]-dione The title compound (193 mg) is obtained in the same manner as in Example 1-(9) as a yellow powder from the compound (220 mg) in the above (1).

M.p. >165° C. (decomposed)

IR (Nujol): $v_{max}^{cm-1}$=3350, 1745, 1660, 1615

Mass: m/z=754 ([M−Cl+H]$^+$)

NMR (300 MHz, d$_6$-DMSO): $\delta^{TMS}$=0.87 (3H, t, J=7 Hz), 1.80–1.94 (2H, m), 2.08–2.27 (2H, m), 2.41 (3H, s), 2.77 (1H, dd, J=13 Hz, 9 Hz), 3.01 (1H, dd, J=13 Hz, 5 Hz), 3.15–3.28 (2H, m), 3.5–3.91 (6H, m), 4.45–4.56 (1H, m), 5.25 (2H, s), 5.41 (1H, d, J=13 Hz), 5.42 (1H, d, J=13 Hz), 5.57 (1H, m), 7.12–7.30 (5H, m), 7.32 (1H, s), 7.80 (1H, d, J=11 Hz), 8.0–8.2 (3H, br), 8.32 (1H, d, J=7 Hz), 8.43 (1H, t, J=5.5 Hz), 8.50–8.62 (2H, m)

(3) Preparation of the Camptothecin Derivative

CM-Dextran sodium salt (CM-degree; 0.65) (2000 mg) and the compound (170 mg) obtained in the above (2) are treated in the same manner as in Example 3-(3) to give the desired camptothecin derivative (1803 mg) as a pale yellow powder. The content of (9S)-1-amino-9-ethyl-5-fluoro-2,3-dihydro-9-hydroxy-4-methyl-1H,12H-benzo[de]pyrano[3',4':6,7]indolidino[1,2-b]quinoline-10,13[9H,15H]-dione hydrochloride in the desired camptothecin derivative is 3.0% which is calculated on the basis of the absorbance at 376 nm. According to the analysis by gel permeation chromatography (GPC), the average molecular weight of the desired camptothecin derivative is 187,000, and the degree of distribution (Mw/Mn) is 1.54.

Conditions for GPC analysis: G4000SWXL (manufactured by Toso, Ltd), 0.2M phosphate buffer (pH 7.0)

EXAMPLES 8–24

The camptothecin derivatives as listed in Table 1 are obtained in the same manner as in Examples 1–6.

TABLE 1

| Ex. No. | R |
|---|---|
| 8 | CM.Dextran.Na-L-Phe- |
| 9 | CM.Dextran.Na-Gly-Gly- |
| 10 | CM.Dextran.Na-L-Leu-Gly- |
| 11 | CM.Dextran.Na-L-Phe-Gly- |

TABLE 1-continued

Structure: R—HN—(CH₂)₃—O—[camptothecin derivative with H₅C₂ and OH]

| Ex. No. | R |
|---|---|
| 12 | CM.Dextran.Na-L-Tyr-Gly- |
| 13 | CM.Dextran.Na-Gly-Gly-Gly- |
| 14 | CM.Dextran.Na-Gly-Gly-Gly-Gly- |
| 15 | CM.Dextran.Na-Gly-Gly-Gly-Gly-Gly- |
| 16 | CM.Pullulan.Na-L-Phe- |
| 17 | CM.Pullulan.Na-Gly-Gly- |
| 18 | CM.Pullulan.Na-L-Leu-Gly- |
| 19 | CM.Pullulan.Na-L-Phe-Gly- |
| 20 | CM.Pullulan.Na-L-Tyr-Gly- |
| 21 | CM.Pullulan.Na-Gly-Gly-L-Phe-Gly- |
| 22 | CM.Pullulan.Na-Gly-Gly-Gly- |
| 23 | CM.Pullulan.Na-Gly-Gly-Gly-Gly- |
| 24 | CM.Pullulan.Na-Gly-Gly-Gly-Gly-Gly- |

[CM-Pullulan.Na: Carboxymethylpullulan sodium salt]

-Gly-Gly-Gly-Gly- is SEQ ID NO:1;
-Gly-Gly-Gly-Gly-Gly- is SEQ ID NO:2; and
-Gly-Gly-L-Phe-Gly- is SEQ ID NO:3

EXAMPLES 25–41

The camptothecin derivatives as listed in Table 2 are obtained in the manner as in Examples 1–6.

TABLE 2

Structure: R—N(piperazine)—CH₂—[camptothecin derivative with dioxane ring, H₅C₂ and OH]

| Ex. No. | R |
|---|---|
| 25 | CM.Dextran.Na-L-Phe- |
| 26 | CM.Dextran.Na-Gly-Gly- |
| 27 | CM.Dextran.Na-L-Leu-Gly- |
| 28 | CM.Dextran.Na-L-Phe-Gly- |
| 29 | CM.Dextran.Na-L-Tyr-Gly- |
| 30 | CM.Dextran.Na-Gly-Gly-Gly- |
| 31 | CM.Dextran.Na-Gly-Gly-Gly-Gly- |
| 32 | CM.Dextran.Na-Gly-Gly-Gly-Gly-Gly- |
| 33 | CM.Pullulan.Na-L-Phe- |
| 34 | CM.Pullulan.Na-Gly-Gly- |
| 35 | CM.Pullulan.Na-L-Leu-Gly- |
| 36 | CM.Pullulan.Na-L-Phe-Gly- |
| 37 | CM.Pullulan.Na-L-Tyr-Gly- |
| 38 | CM.Pullulan.Na-Gly-Gly-L-Phe-Gly- |
| 39 | CM.Pullulan.Na-Gly-Gly-Gly- |
| 40 | CM.Pullulan.Na-Gly-Gly-Gly-Gly- |
| 41 | CM.Pullulan.Na-Gly-Gly-Gly-Gly-Gly- |

-Gly-Gly-Gly-Gly- is SEQ ID NO:1;
-Gly-Gly-Gly-Gly-Gly- is SEQ ID NO:2; and
-Gly-Gly-L-Phe-Gly- is SEQ ID NO:3

EXAMPLES 42–59

The camptothecin derivatives as listed in Table 3 are obtained in the manner as in Examples 1–6.

TABLE 3

Structure: R—NH—[camptothecin derivative with H₅C₂ and OH]

| Ex. No. | R |
|---|---|
| 42 | CM.Dextran.Na-L-Phe- |
| 43 | CM.Dextran.Na-Gly-Gly- |
| 44 | CM.Dextran.Na-L-Leu-Gly- |
| 45 | CM.Dextran.Na-L-Phe-Gly- |
| 46 | CM.Dextran.Na-L-Tyr-Gly- |
| 47 | CM.Dextran.Na-Gly-Gly-L-Phe-Gly- |
| 48 | CM.Dextran.Na-Gly-Gly-Gly- |
| 49 | CM.Dextran.Na-Gly-Gly-Gly-Gly- |
| 50 | CM.Dextran.Na-Gly-Gly-Gly-Gly-Gly- |
| 51 | CM.Pullulan.Na-L-Phe- |
| 52 | CM.Pullulan.Na-Gly-Gly- |
| 53 | CM.Pullulan.Na-L-Leu-Gly- |
| 54 | CM.Pullulan.Na-L-Phe-Gly- |
| 55 | CM.Pullulan.Na-L-Tyr-Gly- |
| 56 | CM.Pullulan.Na-Gly-Gly-L-Phe-Gly- |
| 57 | CM.Pullulan.Na-Gly-Gly-Gly- |
| 58 | CM.Pullulan.Na-Gly-Gly-Gly-Gly- |
| 59 | CM.Pullulan.Na-Gly-Gly-Gly-Gly-Gly- |

-Gly-Gly-Gly-Gly- is SEQ ID NO:1;
-Gly-Gly-Gly-Gly-Gly- is SEQ ID NO:2; and
-Gly-Gly-L-Phe-Gly- is SEQ ID NO:3

EXAMPLES 60–76

The camptothecin derivatives as listed in Table 4 are obtained in the manner as in Examples 1–6.

TABLE 4

Structure: R—NH—CH₂—[camptothecin derivative with dioxane ring, H₅C₂ and OH]

| Ex. No. | R |
|---|---|
| 60 | CM.Dextran.Na-L-Phe- |
| 61 | CM.Dextran.Na-Gly-Gly- |
| 62 | CM.Dextran.Na-L-Leu-Gly- |
| 63 | CM.Dextran.Na-L-Phe-Gly- |
| 64 | CM.Dextran.Na-L-Tyr-Gly- |
| 65 | CM.Dextran.Na-Gly-Gly-Gly- |
| 66 | CM.Dextran.Na-Gly-Gly-Gly-Gly- |
| 67 | CM.Dextran.Na-Gly-Gly-Gly-Gly-Gly- |
| 68 | CM.Pullulan.Na-L-Phe- |
| 69 | CM.Pullulan.Na-Gly-Gly- |
| 70 | CM.Pullulan.Na-L-Leu-Gly- |
| 71 | CM.Pullulan.Na-L-Phe-Gly- |
| 72 | CM.Pullulan.Na-L-Tyr-Gly- |
| 73 | CM.Pullulan.Na-Gly-Gly-L-Phe-Gly- |
| 74 | CM.Pullulan.Na-Gly-Gly-Gly- |
| 75 | CM.Pullulan.Na-Gly-Gly-Gly-Gly- |
| 76 | CM.Pullulan.Na-Gly-Gly-Gly-Gly-Gly- |

-Gly-Gly-Gly-Gly- is SEQ ID NO:1;
-Gly-Gly-Gly-Gly-Gly- is SEQ ID NO:2; and
-Gly-Gly-L-Phe-Gly- is SEQ ID NO:3

EXAMPLES 77–93

The camptothecin derivatives as listed in Table 5 are obtained in the manner as in Examples 1–6.

TABLE 5

[Structure: camptothecin derivative with NH—R, CH$_3$, F substituents, H$_5$C$_2$, OH]

| Ex. No. | R |
|---|---|
| 77 | CM.Dextran.Na-L-Phe- |
| 78 | CM.Dextran.Na-Gly-Gly- |
| 79 | CM.Dextran.Na-L-Leu-Gly- |
| 80 | CM.Dextran.Na-L-Phe-Gly- |
| 81 | CM.Dextran.Na-L-Tyr-Gly- |
| 82 | CM.Dextran.Na-Gly-Gly-Gly- |
| 83 | CM.Dextran.Na-Gly-Gly-Gly-Gly- |
| 84 | CM.Dextran.Na-Gly-Gly-Gly-Gly-Gly- |
| 85 | CM.Pullulan.Na-L-Phe- |
| 86 | CM.Pullulan.Na-Gly-Gly- |
| 87 | CM.Pullulan.Na-L-Leu-Gly- |
| 88 | CM.Pullulan.Na-L-Phe-Gly |
| 89 | CM.Pullulan.Na-L-Tyr-Gly- |
| 90 | CM.Pullulan.Na-Gly-Gly-L-Phe-Gly- |
| 91 | CM.Pullulan.Na-Gly-Gly-Gly- |
| 92 | CM.Pullulan.Na-Gly-Gly-Gly-Gly- |
| 93 | CM.Pullulan.Na-Gly-Gly-Gly-Gly-Gly- |

-Gly-Gly-Gly-Gly is SEQ ID NO:1;
-Gly-Gly-Gly-Gly-Gly- is SEQ ID NO:2; and
-Gly-Gly-L-Phe-Gly- is SEQ ID NO:3

EXAMPLES 94–110

The camptothecin derivatives as listed in Table 6 are obtained in the same manner as in Examples 1–6.

TABLE 6

[Structure: R—NH—(CH$_2$)$_3$—O— camptothecin derivative with H$_5$C$_2$, OH]

| Ex. No. | R |
|---|---|
| 94 | CM.Dextran.Na-L-Phe- |
| 95 | CM.Dextran.Na-Gly-Gly- |
| 96 | CM.Dextran.Na-L-Leu-Gly- |
| 97 | CM.Dextran.Na-L-Phe-Gly- |
| 98 | CM.Dextran.Na-L-Tyr-Gly- |
| 99 | CM.Dextran.Na-Gly-Gly-Gly- |
| 100 | CM.Dextran.Na-Gly-Gly-Gly-Gly- |
| 101 | CM.Dextran.Na-Gly-Gly-Gly-Gly-Gly- |
| 102 | CM.Pullulan.Na-L-Phe- |
| 103 | CM.Pullulan.Na-Gly-Gly- |
| 104 | CM.Pullulan.Na-L-Leu-Gly- |
| 105 | CM.Pullulan.Na-L-Phe-Gly |

TABLE 6-continued

[Structure: R—NH—(CH$_2$)$_3$—O— camptothecin derivative with H$_5$C$_2$, OH]

| Ex. No. | R |
|---|---|
| 106 | CM.Pullulan.Na-L-Tyr-Gly- |
| 107 | CM.Pullulan.Na-Gly-Gly-L-Phe-Gly- |
| 108 | CM.Pullulan.Na-Gly-Gly-Gly- |
| 109 | CM.Pullulan.Na-Gly-Gly-Gly-Gly- |
| 110 | CM.Pullulan.Na-Gly-Gly-Gly-Gly-Gly- |

-Gly-Gly-Gly-Gly- is SEQ ID NO:1;
-Gly-Gly-Gly-Gly-Gly- is SEQ ID NO:2; and
-Gly-Gly-L-Phe-Gly- is SEQ ID NO:3

Reference Example 1

(1) Dextran (Dextran T-110, average molecular weight; 100,000 (by the GPC analysis), manufactured by Pharmacia Biotech AB) (29 g) is dissolved in water (290 ml). To the solution is added sodium borohydride (1.45 g) at 0–5° C., and the mixture is stirred at 5° C. overnight. The pH value of the reaction mixture is adjusted to pH 5 with acetic acid, and the mixture is further stirred at room temperature for 3 hours. The pH value of the mixture is adjusted to pH 7 with 2N aqueous sodium hydroxide solution, and thereto is added ethanol (1.2 L) with vigorously stirring. The mixture is allowed to stand, and the insoluble materials are precipitated. The supernatant of the mixture is removed by decantation, and the residue is centrifuged. The residue is dissolved in water (0.5 L) and the mixture is lyophilized to give a white powder (26.3 g).

(2) The white powder thus obtained (50 g) is dissolved in water (500 ml), and thereto is added sodium hydroxide (200 g) under ice-cooling. The mixture is stirred for 30 minutes, and warmed to room temperature. To the mixture is added dropwise a solution of monochloroacetic acid (110 g) in water (150 ml), and the mixture is stirred at 40° C. for 18 hours. The reaction mixture is cooled to a temperature below 10° C., and the pH value of the mixture is adjusted to pH 8–9 with acetic acid. Methanol (8 L) is added to the reaction mixture with vigorously stirring, and the insoluble materials are precipitated. The insoluble materials are collected by filtration, and dissolved in pure water (5 L). The solution is desalted by ultrafiltration. The residual solution is concentrated under reduced pressure, and filtered. Ethanol is added to the filtrate, and the precipitated material is collected by filtration, washed with aqueous ethanol and acetone, and dried under reduced pressure at room temperature, and then dried under reduced pressure at 50° C. to give carboxymethyl-dextran (CM-dextran) sodium salt (the degree of carboxymethylation by neutralization titration method; 0.5) (50.2 g).

Reference Example 2

CM-Dextran sodium salt having a degree of carboxymethylation of 0.65 is obtained in the same manner as in Reference Example 1 except that the amount of monochloroacetic acid is changed.

What is claimed is:

1. A compound comprising camptothecin of formula (I):

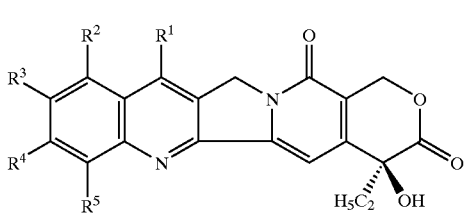

(I)

wherein any two of the substituent variables $R^1$, $R^2$, $R^3$, $R^4$ and $R^5$ that are adjacent to one another combine to form an alkylene group, and the remaining three substituent variables among $R^1$, $R^2$, $R^3$, $R^4$ and $R^5$ are independently selected from the group consisting of a hydrogen atom, an alkyl group or a halogen atom, and wherein one of the carbon atoms of said alkylene group is substituted by a group of the formula $X_n$-$Alk_m R^6$, and wherein one or two methylene groups of the alkylene group may optionally be replaced by —O—, —S— or —NH—; and wherein X is —O— or —NH—, Alk is an alkylene group, $R^6$ is —NHR$^7$, —OR$^7$, or a moiety of the formula:

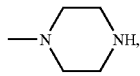

$R^7$ is an amino acid or a peptide, m and n are both 0 or 1, or m is 1 and n is 0; or a salt thereof.

2. The compound according to claim 1, wherein the amino acid or peptide is bonded to the amino or group of the formula

or hydroxy group of $R^6$ via an amide or ester bond, or a salt thereof.

3. The compound according to claim 2, wherein the C-terminal carboxyl group of the amino acid or the peptide is bonded to $R^6$ of the compound (I) through an amide or ester bond, or a salt thereof.

4. The compound according to claim 3, wherein $R^6$ of the compound (I) is —NH$_2$ or a group of the formula:

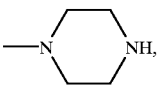

and the compound (I) is bonded to a peptide, or a salt thereof.

5. The compound according to claim 4, wherein $R^1$ and $R^2$ combine to form an amino-substituted trimethylene group, $R^3$ is a methyl group, $R^4$ is a fluorine atom, $R^5$ is a hydrogen atom; or a salt thereof.

6. The compound according to claim 5, wherein the peptide is a member selected from the group consisting of SEQ ID NO:3, SEQ ID NO:4, glycyl-glycine, glycyl-glycyl-glycine, SEQ ID NO:1, SEQ ID NO:2, L- or D-phenylalanyl-glycine and L- or D-leucyl-glycine, or a salt thereof.

7. The compound according to claim 6, wherein the peptide is glycyl-glycyl-glycine, or a salt thereof.

8. The compound according to claim 6, wherein the peptide is SEQ ID NO:3, or a salt thereof.

9. The compound according to claim 6, wherein the peptide is SEQ ID NO:1, or a salt thereof.

10. The compound according to claim 6, wherein the peptide is glycyl-glycine, or a salt thereof.

11. The compound according to claim 6, wherein the peptide is L- or D-phenylalanyl-glycine, or a salt thereof.

12. A compound according to the following formula:

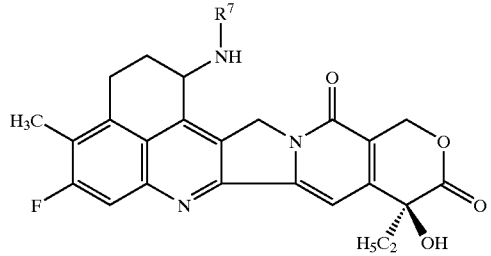

wherein $R^7$ is an amino acid or a peptide, and wherein the C-terminal carboxyl group of said amino acid or peptide is bonded to the amino group via an amide bond; or a salt thereof.

* * * * *

SEQUENCE LISTING

<160> NUMBER OF SEQ ID NOS: 4

<210> SEQ ID NO 1
<211> LENGTH: 4
<212> TYPE: PRT
<213> ORGANISM: Artificial
<220> FEATURE:
<223> OTHER INFORMATION: Peptide which intervenes between a camptothecin
      compound [I] and a polysaccharide having carboxyl groups

<400> SEQUENCE: 1

Gly Gly Gly Gly
1

<210> SEQ ID NO 2
<211> LENGTH: 5
<212> TYPE: PRT
<213> ORGANISM: Artificial
<220> FEATURE:
<223> OTHER INFORMATION: Peptide which intervenes between a camptothecin
      compound [I] and a polysaccharide having carboxyl groups

<400> SEQUENCE: 2

Gly Gly Gly Gly Gly
1               5

<210> SEQ ID NO 3
<211> LENGTH: 4
<212> TYPE: PRT
<213> ORGANISM: Artificial
<220> FEATURE:
<223> OTHER INFORMATION: Peptide which intervenes between a camptothecin
      compound [I] and a polysaccharide having carboxyl groups
<220> FEATURE:
<221> NAME/KEY: misc_feature
<222> LOCATION: (3)..(3)
<223> OTHER INFORMATION: L-Phenylalanyl residue

<400> SEQUENCE: 3

Gly Gly Phe Gly
1

<210> SEQ ID NO 4
<211> LENGTH: 4
<212> TYPE: PRT
<213> ORGANISM: Artificial
<220> FEATURE:
<223> OTHER INFORMATION: Peptide which intervenes between a camptothecin
      compound [I] and a polysaccharide having carboxyl groups
<220> FEATURE:
<221> NAME/KEY: misc_feature
<222> LOCATION: (3)..(3)
<223> OTHER INFORMATION: D-Phenylalanyl residue

<400> SEQUENCE: 4

Gly Gly Phe Gly
1